United States Patent [19]

Loran

[11] 4,280,995

[45] Jul. 28, 1981

[54] ORAL SUSPENSION OF PHENYTOIN

[75] Inventor: Muriel R. Loran, New York, N.Y.

[73] Assignee: Pharmaceutical Associates, Inc., Tampa, Fla.

[21] Appl. No.: 108,345

[22] Filed: Dec. 31, 1979

[51] Int. Cl.$^3$ .................. A61K 31/70; C07H 17/00
[52] U.S. Cl. ........................................ 424/180; 536/1; 536/18; 536/23; 424/314; 424/273 R
[58] Field of Search ................... 424/180, 273 R; 548/314; 536/1, 18, 23

[56] References Cited

U.S. PATENT DOCUMENTS 4,163,058  7/1979  Stella et al. .................. 424/273 R Primary Examiner—Delbert R. Phillips
Assistant Examiner—Blondel Hazel
Attorney, Agent, or Firm—Arthur W. Fisher, III

[57] ABSTRACT

The invention comprises a 5,5-diphenyl-2,4-imidazolidinedione-guaran complex formed by reacting an aqueous solution of guaran with an organic solvent solution of 5,5-diphenyl-2,4-imidazolidinedione. The invention also includes a therapeutic composition and method wherein the active agent is the guaran 5,5-diphenyl-2,4-imidazolidinedione complex.

11 Claims, No Drawings

ORAL SUSPENSION OF PHENYTOIN

BACKGROUND OF THE INVENTION

The present invention relates to a new compound comprising the reaction product of guaran and 5,5-deiphenyl-2,4-imidazolidinedione (phenytoin).

Phenytoin, commonly known as dilantin, is 5,5-phenyl-2,4-imidazolidinedione and is a well known therapeutic agent useful as an anti-convulsant effective for the treatment of generalized tonic-clonic seizures ("grand mal") in adults and children, and is also useful in the treatment of simple and complex partial seizures ("focal" and "tempral lobe and psychomotor").

5,5-diphenyl-2,4-imidazolidinedione and methods for its production are described in U.S. Pat. No. 2,409,754. The pharmacology of phenytoin in *Anticonvulsants*, Vida, Julius A. Ed. 176-284, Academic Press, New York, 1977.

Phenytoin or 5,5-dipenyl-2,4imidazolidinedione, is practically insoluble in water and is soluble in alcohol to the extent that one gram dissolves in about 60 ml of absolute alcohol. Numerous attempts have been made to dissolve or otherwise suspend 5,5-diphenyl-2,4-imidazolidinedione in water and other common pharmaceutically acceptable carriers; however, because of the hydrophobicity of this compound (phenytoin) none has provided sufficient reduction in particle size to allow the absorption of phenytoin, or sufficiently homogeneous suspension to allow for uniformity of dosage. In addition, not only must this compound be absorbed but it must be absorbed in such a way as to produce predictable and sustainable blood levels.

For example, the use of commonly employed high molecular weight suspending agents, which depend on viscosity to suspend the hydrophobic particles of phenytoin, result in suspensions which do not suspend since the phenytoin remains in the crystalline form and floats on the surface of such suspensions. Phenytoin is hydrophobic because of the strong intermolecular bonding of the phenytoin molecules one to the other, resulting in a crystal lattice structure that has a melting point of 295°-298° C. The phenytoin crystal structure is such that bonding between molecules creates a rigid polymer. Phenytoin is capable of bonding to cellulose polymers through electrostatic interaction, however such complexes do not allow the release of the phenytoin as they travel through the gastrointestinal tract. Since the polymer is not degraded into smaller units within the gastrointestinal tract, the phenytoin would remain with the polymer. In order for absorption to occur from such a polymer, the polymer must be subdivided to units which combined with the phenytoin must not exceed a molecular weight of 700-900. Cellulose polymers have molecular weights ranging in the hundred of thousands, and are not degraded in the gastrointestinal tract.

To date, there has been no satisfactory solution of the problem of forming a suitable pharmaceutically acceptable preparation of phenytoin which is easily administered yet capable of allowing the transport of phenytoin across the intestinal mucosa.

It is an object of the present invention to provide an easily suspended compound, one which results from the molecular interaction of phenytoin with a hydrophillic macromolecule which is degradable within the gastrointestinal tract. This resultant new macromolecular species bearing the active phenytoin component with it, may then be administered in a dosage form to animals and humans which results in the absorption of phenytoin at a therapeutically desireable rate and allows for the sustenance of therapeutic blood levels, while minimizing the possibility of toxic events.

SUMMARY OF THE INVENTION

The present invention comprises a new compound of 5,5-diphenyl-2,4-imidazolidinedione and guaran, formed by intimately admixing an aqueous solution of guaran, and 5,5-diphenyl-2,4-imidazolidinedione in a quasi solution phase, of absolute alcohol and sorbitol. The hydroxyls present in ethyl alcohol and sorbitol allow disruption of the tight crystal lattice structure of the phenytoin, allowing for combination with the guaran.

This resultant compound referred to herein as guaran diphenylhydantoinate can then be administered to animal or human.

DETAILED DESCRIPTION OF THE INVENTION

It has been found that guaran forms a true compound with 5,5-diphenyl-2,4-imidazolidinedione. Although guaran has a molecular weight of approximately two hundred and fifty thousand, the compound formed with 5,5-diphenyl-2,4-imidazolidinedione does not suffer from the disadvantages associated with the large molecular weight suspending agents utilized heretofore. Guaran is comprised of a long chain of (1-4) -beta-D-mannopyranosyl units with alpha-D-galactophyranosyl units attached by (1-6) linkages; the ration of D-galactose: D-mannose being 1:2. The guaran is broken down by enzymes existing in the gastrointestinal tract into sub units which combined with phenytoin reach a molecular weight not greater than 700-900 which is below the maximum limit for absorption in the small intestine.

The combination of guaran with 5,5-diphenyl-2,4-imidazolidinedione results in the formation of a compound which is easily dissolved and/or suspended in, for example, aqueous alcoholic solutions thereby rendering it easily administerable to animals and humans. Even though the guaran is chemically combined with the phenytoin molecule, it is readily broken down in the small intestine to molecular units having a molecular weight of less than 700-900, thereby permitting its ready absorption by the intestine.

The guaran actually functions as a protective agent for the phenytoin molecule during its passage through the body to the small intestine, the two resulting in a hydrophobic/hydrophillic balance. The compound is thereby tasteless, and the irritant properties of phenytoin alone are not manifested in the mouth or stomach on its passage to the small intestine. No other suspending or complexing agent utilized heretofore combines this dual function of protection and ready release of active component.

The new compound enables a homogeneous and uniform dispersion of the phenytoin throughout the suspension, thereby ensuring a uniform dosage in each and every unit of the composition. Since the phenytoin molecule cannot appear in the bloodstream until absorption results from the breakdown of the guaran of the component of the compound, the rate of absorption or appearance in the bloodstream would depend on the enzymatic degradation of guaran. In other words the rate-limiting factor in absorption would be enzymatic degradation of the macromolecular compound.

In order to obtain a steady sustained release action it is necessary that the rate of absorption substantially equal the rate of elimination of the guaran and degradation products thereof. Phenytoin is hydroxylated and eliminated through the liver.

It has been found that the rate of degradation of this compound is equal to the rate of elimination of phenytoin from the body. Analysis of blood levels has shown that after the compound is administered a steady state of phenytoin in the blood is maintained for 12 to 24 hours following a single minimal dose (1 mg./Kg.). This level does not fluctuate but remains at this steady state. In order for this to obtain, the rate of absorption of the phenytoin must equal the rate of elimination.

Phenytoin elimination occurs after parahydroxylation of phenytoin by the P-450 enzymes of the liver mitochondria; the resultant parahydroxylated metabolite is excreted in the urine. Enzymatic breakdown before absorption and enzymatic transformation prior to elimination must therefore occur at similar rates.

The compound is formed by intimately admixing an aqueous solution of guaran with a quasi solution of phenytoin in alcohol and sorbitol. Ethanol is used to break down the particle size of phenytoin by disrupting the tight crystal lattice structure, sorbitol is then added to disperse the phenytoin particles. Following this the solution of guaran is added and immediate compound formation is evidenced by the formation of a rigid gel. Gel formation is a result of cross-linking of guaran by the phenytoin molecules. Upon mechanical agitation the gel becomes fluid again and the compound is dispersed in the aqueous medium.

The rigid gel probably exists in the "egg box" configuration, and the energy provided by additional agitation reorients the hydrophyllic groups toward water while the hydrophobic backbone orients internally. In addition to hydrogen bonding, coordinate and or covalent bonding is probable. Phenytoin is capable of hydrogen bonding and covalent and coordinate bonding, guaran is a macromolecule capable of cross-linking. The resultant compound consisting of a molar ration of phenytoin:guaran of 1000:1 is hydrophillic in aqueous systems, but will pass into ether completely when there is an ether:water ratio of 20:1. The macromolecular compound can be extracted from an aqueous phase by ether. The compound when in an aqueous phase shows four phase transitions when titrated with a 0.1 N sodium hydroxide. These phase transitions are seen both visually and by plateau and inflection points when measuring pH change upon titration from pH 6 to 12.

The method of the invention is illustrated by the following example:

EXAMPLE 700 ml. of distilled water are placed in a flask equipped with a magnetic stirrer and 1 gram of sodium benzoate added thereto. After dissolution of the sodium benzoate the solution is transferred to a stainless steel container and an electric stirrer is used to create a vortex. Ten grams of guaran is then added into the vortex created by the stirrer and the solution is stirred until the guaran is completely dissolved. The volume of the solution is made up to 1 liter and the solution allowed to stand for 24 hours to release entrapped air. After standing the solution is again made up to 1 liter.

10 grams of 5,5-diphenyl-2,4-imidazolidinedione is triturated with 50 ml. of anhydrous ethanol. Trituration is continued until the phenytoin particles are homogeneous in size. To the resultant phenytoin-alcohol mixture is added while stirring 400 ml. of a 70% solution of sorbitol (Finn fructose solution may be substituted for the sorbitol). Thereafter while stirring, 400 ml. of the 1% guaran solution is added. Partial solidification occurs at this juncture, indicating the formation of a chemical compound. Upon further stirring, the gel redisperses in the aqueous phase. Thereafter, sufficient distilled water is added to make 1 liter of final product.

The suspension may be administered to humans or animals in the form prepared above or the compound may be isolated and compounded with other pharmaceutically acceptable carriers for administration for therapeutic purposes. The compound may be administered in dosages commonly employed for phenytoin alone since the phenytoin in its entirety is released in the intestine for absorption by the host. It is to be understood that the compound may be administered and utilized in the same manner as commonly and conventionally employed compositions containing phenytoin.

What is claimed is:

1. A compound comprising the reaction product prepared by intimately admixing an aqueous solution of guaran and a solution or dispersion of 5,5-diphenyl-2,4-imidazolidinedione.

2. A method for preparing a complex comprising the reaction product of 5,5-diphenyl-2,4-imidazolidinedione and guaran comprising intimately admixing an aqueous solution of guaran and a solution of dispersion of 5,5-diphenyl-2,4-imidazolinedione in an organic solvent capable of disrupting the crystal lattice structure thereof.

3. The method of claim 2 including the step of isolating said reaction product.

4. The method of claim 2 wherein said organic solvent comprises ethanol.

5. The method of claim 2 wherein said aqueous solution contains 10 g/l guaran.

6. A composition in dosage form comprising an anticonvulsant effective amount of the product of claim 1 and a pharmaceutically acceptable carrier.

7. The composition of claim 6 additionally containing a pharmaceutically acceptable sweetner.

8. The composition of claim 7 wherein said sweetner is sorbitol or fructose.

9. A method for reducing the severity of generalized tonic-clonic seizures and complex partial seizures in animals and humans comprising administering to an animal or human in need thereof an anti-convulsant effective amount of the product of claim 1.

10. The method of claim 9 wherein said product is administered orally.

11. The method of claim 9 wherein said product is administered at a dosage of about 1 mg/kg of body weight of said animal or human.

* * * * *